(12) United States Patent
Sovak et al.

(10) Patent No.: US 6,184,249 B1
(45) Date of Patent: Feb. 6, 2001

(54) ANDROGEN RECEPTOR SUPPRESSORS IN THE THERAPY AND DIAGNOSIS OF PROSTATE CANCER, ALOPECIA AND OTHER HYPER-ANDROGENIC SYNDROMES

(75) Inventors: Milos Sovak, La Jolla; Allen L. Seligson, San Marcos; James Gordon Douglass, III, San Diego; Brian Campion, Leucadia; Jason W. Brown, San Diego, all of CA (US)

(73) Assignee: Biophysica, Inc., La Jolla, CA (US)

( * ) Notice: Under 35 U.S.C. 154(b), the term of this patent shall be extended for 0 days.

(21) Appl. No.: 09/215,351

(22) Filed: Dec. 18, 1998

(51) Int. Cl.⁷ .................... A61K 31/275; C07C 255/03; C07C 233/03

(52) U.S. Cl. .................... 514/520; 514/522; 514/596; 558/413; 558/423; 564/154; 564/155; 564/157

(58) Field of Search .................... 558/413, 423; 564/154, 155, 157; 514/520, 522, 596; 424/1.85

(56) References Cited

U.S. PATENT DOCUMENTS

| | | |
|---|---|---|
| 4,636,505 | 1/1987 | Tucker . |
| 4,880,839 | 11/1989 | Tucker . |
| 5,656,651 | 8/1997 | Sovak et al. . |

FOREIGN PATENT DOCUMENTS

| | | |
|---|---|---|
| 2059872 | * 5/1970 | (DE) . |
| 83303998 | 8/1987 | (EP) . |
| WO 97/00071 | 1/1997 | (WO) . |

* cited by examiner

*Primary Examiner*—Floyd D. Higel
*Assistant Examiner*—Ebenezer Sackey
(74) *Attorney, Agent, or Firm*—Bertram I. Rowland; Rae-Venter Law Group, P.C.

(57) ABSTRACT

Substituted phenylalanines are provided comprising an hydantoin, urea or 2-hydroxyl, 2-methylpropionyl group, dimers thereof and alkyl, polyfluoroamido and haloarylamino derivatives thereof, as well as radiolabeled derivatives thereof. The compounds bind specifically to the androgen receptor and find use in the therapy of indications associated with the androgen receptor, such as, hirsutism, acne and androgenetic alopecia, and in the therapy and diagnosis of cell hyperplasia dependent on androgens.

7 Claims, No Drawings

ANDROGEN RECEPTOR SUPPRESSORS IN THE THERAPY AND DIAGNOSIS OF PROSTATE CANCER, ALOPECIA AND OTHER HYPER-ANDROGENIC SYNDROMES

TECHNICAL FIELD

The field of this invention is compounds and their use in the treatment of prostate cancer and hyper-androgenic syndromes including alopecia, hirsutism and acne vulgaris.

BACKGROUND

The existence of a number of pathologic syndromes depends on androgen hormones. Thus, growth of prostate cancer in early stages is androgen driven and can, at least temporarily, be stopped by androgen deprivation. Androgenic alopecia is caused by an unexplained switch from the growth promoting effect of androgens on the hair follicles to hair loss. In skin androgen mediated disorders, such as alopecia, acne vulgaris, and hirsutism, excess of the cutaneous androgens were shown to be the major nosological factor.

The androgenic hormones can act only via an androgenic receptor (AR), which is a transcription factor, a protein which interacts with a specific region of DNA. Thus, the mode of action of testosterone and its much more potent analog, 5-alpha dihydrotestoterone (DHT) depends upon binding to the AR. Only then can transcription by RNA polymerase II take place.

In the treatment of androgenic alopecia, various antiandrogens originally developed for the treatment of prostate cancer were claimed for systemic use, but side effects of chronic therapy with these systemically absorbable substances were of concern. In cutaneous afflictions topical anti-androgenic compositions have been tried, but with limited success, possibly because all non-steroidal compounds are resorbed by the skin and elicit systemic effects, which prevents their use in males. In the scalp, the precursors to androgens are normally converted into potent androgens, which bind to the AR in the hair follicles and promote hair growth. In genetically pre-disposed subjects however androgens at certain age cause hair loss. Clearly, a topically active composition capable of cutaneous, but not systemic resorption, and of suppressing or eliminating the AR locally, would be useful in preventing or reversing the incipient hair loss.

The current state of prostate cancer therapy (CaP), the second most prevalent malignancy in males, is unsatisfactory. When detected early, with the tumor strictly confined to the prostate gland, CaP can be often controlled by implantation of radioactive seeds, or by prostatectomy, which often results in incontinence and impotence. Locally advanced prostate cancer can often be reasonably controlled when in the pelvis and if encompassed into a single port of an external radiation beam.

For advanced CaP, the standard treatment is androgen receptor-blockade, usually in combination with LHRH superagonists, which suppresses both adrenal and testicular testosterone. The rationale of this approach is that early prostate cancer invariably depends on androgens for growth. The activity mechanism of clinically utilized antiandrogens is thought to involve blockade of the AR by binding to it and/or by interference with binding of the AR to the DNA; some agonistic compounds can even promote DNA binding but they do modify the binding domain. Thus, cyproterone acetate was found to block about 50% of AR binding to the DNA, while flutamide, bicalutamide or nilutamide, were found to completely block such binding. All of these state of the art compositions have nevertheless only limited applicability, as the primary tumor and its metastases eventually become refractory to further anti-androgenic therapy. The reason is invariably AR mutation, which can be occasionally found as a genetic deviation, but is usually a result of the AR blockade. Even when both suprarenal and testicular androgens are eliminated by chemical castration, LHRH super agonist and/or by surgical castration, the mutated receptor retains the capability to be activated by various steroidal metabolites and even progestins and estrogens. A variety of other factors can activate the androgen receptor gene via AR activation, such as insulin-like growth factor, epidermal growth factor, and keratinocyte growth factor and neuroendocrine transmitters, such as serotonin. Therefore, blocking the AR is not an ideal treatment and a new approach is needed. It has also been shown that as a result of the AR blockade, the AR gene is amplified with the resulting overproduction of the AR. In 6 to 24 months the AR mutates and the tumor and metastases became hormone refractory and continue to grow.

In selecting therapeutic options, a correct decision can only be made if the extent of the disease is known. When CaP is confined strictly to the gland, surgery and/or local or external radiation can be curative. However, in the case of extracapsular disease, prostatectomy or radiation are not only useless, but noxious, since a high rate of serious side effects, such as impotence, incontinence and chronic inflammation of the adjacent tissues accompanies these interventions. Members of the current diagnostic armamentarium comprise digital rectal palpation, serum prostate specific antigen determination and ultrasound, magnetic resonance or x-ray imaging. These techniques cannot detect CaP metastases to the lymph nodes and other soft tissues, resulting in clinical understaging of 40 to 60% of the patients.

The prior art of diagnostic localizing agents for CaP teaches specific radioactively labeled antibodies, but widespread use is limited by the complexity of the procedure. 5α-dihydrotestosterone labeled with $^{18}F$ has been used for PET scanning, a generally inaccessible imaging modality.

There are substantial deficiencies in both therapeutic and diagnostic approaches to the treatment of CaP. It is therefore of interest to find compounds which not only block the AR, but also diminish the number of available ARs. Another desirable characteristic for topical purposes would be compounds which have low or no systemic resorption. Also, the compounds should degrade or be metabolized into components of low or no toxicity and have little or no anti-androgenic activity. In addition, radioisotope labeled compounds specific for neoplastic prostate cells would be of importance in order to visualize the pathomorphology of CaP accurately, so that unnecessary and costly surgery and/or radiation is avoided in patients where CaP has progressed beyond the reach of curative surgery or the scope of a single radiation port. Other appropriate therapies, such as androgen ablation and/or unspecific chemotherapy, can then be instituted.

Relevant Literature

U.S. Pat. No. 5,656,6651 and WO97/00071, and references cited therein, describe anti-androgenic directed compositions based on phenyldimethylhydantoins, where the phenyl group is substituted with a trifluoromethyl group and either a cyano or nitro group. See also, Battmann et al., J. Steroid Biochem. Molec. Biol. 64:103–111 (1998); Cousty-Berlin, ibid 51:47–55 (1994); and Battmann et al., ibid 48:55–60 (1994), for a description of analogous compounds and their activity. For other compounds having the substituted phenyl moiety, see U.S. Pat. Nos. 4,636,505 and 4,880,839, and EP 0 100 172. For discussions about the activities of antiandrogens, see Kuil and Brinkmann, Eur. Urol. 29:78–82 (1996); Kondo et al., Prostate 29:146–152 (1996), and Simard, et al., Urology 49:580–589 (1997). For discussions about alopecia and its relationship with androgens, see Kaufman, Dermatologic Clinics 14:697–711 (1996); Toney et al., J. Steroid Biochem. Molec. Biol. 60:131–136 (1997); Brouwer et al., J. of Dermatology 137:699–702 (1997); and Shapiro and Price Dermatologic Clinics 16:341–356 (1998).

SUMMARY OF THE INVENTION

Compositions and their method of use are provided, where the compositions are substituted-phenyl-2-methyl,2-(hydroxy or methyl)-3-heteroatom substituted-propionamide derivatives, having heterolinked perfluoroacyl or haloaryl substituents or being bis-derivatives, where the substituent group may be linked to the heteroatom directly or by a linking group. The compounds are active anti-androgenic compounds and find use in the treatment of neoplasms and alopecia dependent on androgen hormones. In addition, the compounds may be radioisotope labeled for use in therapy and/or diagnosis.

DESCRIPTION OF THE SPECIFIC EMBODIMENTS

Compositions are provided, characterized by having an aniline group which has at least one substituent at the para position, desirably a second substituent at the meta position, and to which the aniline nitrogen is bonded a 2-methyl,2-(hydroxy or methyl)-3-heteroatom substituted-propionyl or N-substituted cabamoyl, particularly thiocarbamoyl. The heteroatom (including the nitrogen of the carbamoyl group) is linked through a bond or linking group to a perfluoroacyl, haloaryl, or alkyl substituent or to a divalent linking group to form a bis-compound. The compounds have individual or collective characteristics associated with cellular toxicity, diminution of androgen receptors on the surface of cells and low systemic resorption when administered topically. In addition, the compounds may be radioisotope labeled, to be used in diagnosis and/or therapy.

The monomeric compounds will generally be of from at least 12 carbon atoms, usually at least 14 carbon atoms, more usually of at least 16 carbon atoms and not more than about 36 carbon atoms, usually not more than about 28 carbon atoms, while the bis-compounds will usually be at least 20 carbon atoms, usually at least 22 carbon atoms and not more than about 40 carbon atoms, usually not more than about 36 carbon atoms.

The two position of the propionamide has two methyl groups or one methyl and one hydroxy group. The perfluoroacyl group will be linked to the 3-heteropropionamide through the heteroatom by a bond or a linking group of from 1 to 10, usually 2 to 8 carbon atoms and from 0 to 6, usually 0 to 4, more usually 0 to 2 heteroatoms in the chain of the linking group. The linking group may be aliphatic, alicyclic, heterocyclic or aromatic, usually aliphatic, more usually saturated aliphatic.

For the most part, the compounds of this invention will have the following formula:

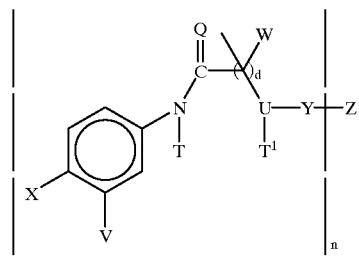

wherein:

Q is chalcogen (oxygen or sulfur);

X is nitro ($NO_2$), cyano (CN), or halogen, particularly of from atomic no. 9 to 35, particularly 9 to 17 (fluorine and chlorine);

V is $CF_3$, halogen, particularly of from atomic no. 9 to 35, particularly 9 to 17 (fluorine and chlorine) or H; usually $CF_3$;

T is hydrogen or is taken together with $T^1$ to form a C=Z bridge, where Z is chalcogen of atomic number 8 to 16 (oxygen {carbonyl} or sulfur {thiocarbonyl}), particularly sulfur;

W is OH when T is H and methyl when T and $T^1$ are C=Z;

U is N when T and $T^1$ are taken together to form a C=Z bridge or when d is 0, and is otherwise taken together with $T^1$ to form a bond or NH, S or O, particularly NH and S;

n is 1 or 2 and d is 0 or 1;

when d is 0, T and $T^1$ are hydrogen;

when d is 1, then:

when n is 1 or when d is 0, Y is a bond or linking group of from 1 to 10, frequently 0 to 8 carbon atoms, usually 2 to 8, more usually 2 to 6 carbon atoms and from 0 to 6, usually 0 to 4 heteroatoms, with from 0 to 4 heteroatoms in the chain, where the heteroatoms are N, O, S, and the heteroatoms are present as amino (includes amido), oxy and oxo- and non-oxo-carbonyl, and thio and thiono- and non-thiono-carbonyl, where the linking group may be aliphatic, alicyclic, heterocyclic or aromatic, usually aliphatic, usually saturated; and Z, when not taken together with Y, is an aliphatic group of from 1 to 10, usually 1 to 6, more usually 1 to 5 carbon atoms, saturated or unsaturated, e.g. double or triple bond, polyfluoroacylamido group of from 2 to 10, frequently of 2 to 8, usually 2 to 6, more usually 3 to 5 carbon atoms and having at least 2 fluoro groups and a total of 2m−1 fluoro groups, usually having at least 2m−2 fluoro groups, wherein m is the number of carbon atoms, or substituted arylamino of from 6 to 12, more usually 6 to 10 carbon atoms, particularly anilino, and halogen of atomic number from 9 to 80, particularly F, Cl, Br and I, more particularly Br and I (atomic no. 35 to 80), particularly para substituted;

when n is 2, Y and Z are taken together to form a bond or a linking group of a total of from 1 to 10, usually 1 to 8 atoms, having 0 to 10, usually 0 to 8 carbon atoms, more usually 2 to 6 carbon atoms and from 0 to 6, usually 0 to 4 heteroatoms, with from 0 to 4, usually 0 to 2, heteroatoms in the chain, where the heteroatoms are N, O, S, there being at least one carbon atom or heteroatom in the linking group, and the heteroatoms are present as amino (includes amido), oxy and oxo- and non-oxo-carbonyl, and thio and thiono- and non-thiono-carbonyl, where the linking group when other than 1 heteroatom may be aliphatic, alicyclic, heterocyclic or aromatic, usually aliphatic, usually saturated; and the phenyl group, Y and/or Z may be substituted with convenient radiolabel, particularly Z, where the label may be radioactive iodine, a chelated metal, e.g., technetium, or other suitable emitter.

When Y is a bond, U will also usually be a bond, so as to join the nitrogen of the polyfluoroacylamido or anilino group to the propionyl carbon atom.

For radiolabeling, Z may have different convenient functionalities depending on the nature of the radiolabel. For example, with radioactive iodine, one may use an acetylenic group for addition a hydride, e.g. a tin hydride, followed by substitution of the tin group with iodine. Where the radiolabel is chelated, the chelating group may be attached to Z by any convenient functionality, such as an amide group, ester, ether, thioether, amino, etc. Chelating compounds include combinations of imidazoles, thiolacetic acids, cysteine, glycineamides, etc.

The compounds may or may not have one or more stereoisomeric centers. The compounds may be used as racemic mixtures or be resolved in their enantiomers and used as enantiomers.

When the compounds have the hydantoin ring, they will usually come within the following formula:

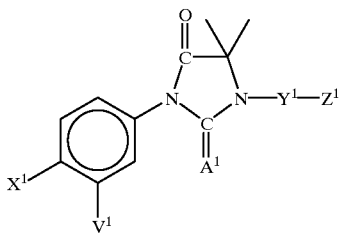

wherein:

$X^1$, $V^1$, and $Y^1$ come within the definitions of X, V and Y, respectively;

$Y^1$ is usually alkylene of from 2 to 10, usually 2 to 8, more usually 2 to 6, carbon atoms;

$A^1$ is chalcogen (oxygen or sulfur), particularly sulfur; and $Z^1$ is a polyfluoroacylamido of from 2 to 10, usually 2 to 6, more usually 3 to 5 carbon atoms and having at least 2 fluoro groups and not more than 2m−1 fluoro groups, usually having at least 2m−2 fluoro groups, wherein m is the number of carbon atoms, or substituted arylamino of from 6 to 12, more usually 6 to 10 carbon atoms, particularly anilino, and halogen of atomic number from 9 to 80, particularly F, Cl, Br and I, more particularly Br and I (atomic no. 35 to 80) preferably para-substituted Those compounds which have an 2-hydroxy,2-methylpropionyl group as a moiety will for the most part have the following formula:

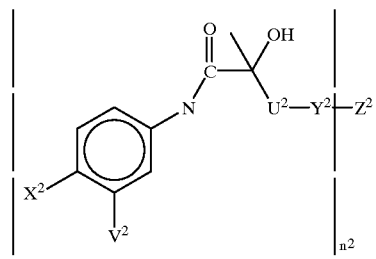

wherein:

$X^2$, $V^2$ and $n^2$ come within the definitions of X, V and n, respectively;

$U^2$ is a bond or heteroatom, particularly nitrogen and chalcogen (O and S); when $n^2$ is 1;

$Y^2$ is an alkylene group of from 1 to 10, usually 1 to 6 carbon atoms, more usually 2 to 6 carbon atoms and 0 to 4 heteroatoms, which heteroatoms are N and chalcogen and include the functional groups carbonyl, thiocarbonyl, oxy, thio, and amino; and $Z^2$ is a polyfluoroacylamido of from 2 to 10, usually 2 to 6, more usually 2 to 4 carbon atoms and having at least 2 fluoro groups and not more than 2m−1 fluoro groups, usually having at least 2m−2 fluoro groups, or substituted arylamino of from 6 to 12, more usually 6 to 10 carbon atoms, particularly phenyl, and halogen of atomic number from 9 to 80, particularly F, Cl, Br and I, more particularly Br and I, preferably para substituted.

The compounds which have the carbamoyl group, will for the most part have the following formula:

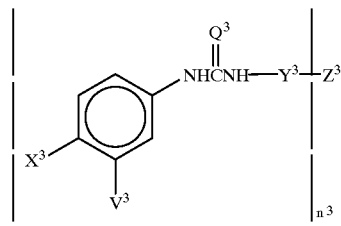

wherein:

$X^3$ and $V^3$ come within the definitions of $X^1$ and $V^1$;

$Q^3$ is chalcogen, particularly sulfur;

$Y^3$ is a bond or alkylene group of from 1 to 6, usually 1 to 3 carbon atoms;

$Z^3$ is alkyl of from 1 to 6 carbon atoms, a polyfluoroacylamido of from 2 to 10, usually 2 to 6, more usually 2 to 4 carbon atoms and having at least 2 fluoro groups and not more than 2m−1 fluoro groups, usually having at least 2m−2 fluoro groups, or substituted arylamino of from 6 to 12, more usually 6 to 10 carbon atoms, particularly phenyl, and halogen of atomic number from 9 to 80, particularly F, Cl, Br and I, more particularly Br and I, preferably para substituted.

The subject compounds can be prepared in accordance with conventional ways, varying the particular procedure based on the particular side groups. The preparation of hydantoins conveniently involves the use of an isocyanate and a substituted α-aminoacetonitrile. By appropriate choice of the isocyanate and the α-aminoacetonitrile, one may arrive at the final product in a single step. Alternatively, one may employ various protective groups, which may be subsequently removed or provide for substituents which become involved in the formation of the hydantoin or may provide for sites for further derivatization. Various procedures are described in EPO Publication nos. 0 494 819 and 0 580 459. The urea compounds may be prepared using an isocyanate (including thioisocyanate) and an amino compound. A significant number of examples are provided for the hydantoins and the propionyl moiety compounds in the experimental section of this application.

The subject compounds can be used as antiandrogens, substituting for known antiandrogens in the treatment of proliferative diseases, hirsutisim, acne and androgenetic alopecia. The subject compounds display one or more of the following properties: specific binding and high affinity to the androgen receptor; destroying or suppressing the presence of the androgen receptor in a concentration dependent fashion; low or no systemic resorption when applied topically; and limited stability, degrading into components of low toxicity and no androgenic activity. The subject compounds may be used individually or in combination and with other antiandrogens or other treatments, such as flutamide, bicalutamide and nilutamide, irradiation, heat, or the like, as may be conventionally employed and as may be moderated for use in conjunction with the subject compounds. The treatments may be performed concurrently, consecutively or in accordance with a predetermined regimen to minimize the likelihood of neoplastic cell refractoriness.

The subject compounds are found to have high cytostatic and cytotoxic activity, inhibiting cell growth and viability of cells having an androgen receptor. They also have substantially greater effect against neoplastic cells, as compared to normal cells.

Therapeutic compositions can be formulated in accordance with conventional ways and the indication to be treated. The composition may be formulated for oral or parenteral, e.g. intravascular, subcutaneous, intratumoral, intraperitoneally, etc., administration, as a pill, powder, capsule, aqueous or oily solution or dispersion, or the like. Conventional carriers include saline, phosphate buffered saline, water, vegetable oils, ethanol, isopropanol, etc. Excipients, buffers, stabilizers, flavorings or the like may be employed. The concentration may be from about 0.1 to 10 weight % and at a dosage in the range of about 0.10 mg to about 5 g, usually not more than about 2 g/dose. One or more doses may be given daily.

The subject compounds may be used in conjunction with conventional therapeutic agents for a specified treatment, being used in combination with anti-neoplastic agents, agents for the treatment of alopecia, etc. Of particular interest is to employ a regimen where the subject compound is used with an agent for treating alopecia, such as Minoxidil® or Aminexil® (a trademark of L'Oreal), where the dosage employed for the known agent may be the same as in the absence of the subject compound or may be reduced based on the observed experience with the combination. Determining the optimum dosage for the combination can be done in conventional ways using appropriate clinical studies and varying ratios of the two ingredients, which may be in a common formulation or employed as two independent formulations.

The subject compounds may be used in competitive assays or as controls for evaluating other compounds as to their cytostatic or cytotoxic effect or for blocking the androgen receptor. Thus, specific cell lines may be employed where the effect of an agent on the activity of a subject compound may be determined in relation to the survival rate or other indicia of the target cells. Also, in mixtures of cells containing neoplastic androgenic receptor containing cells, the subject compounds can be used to eliminate the neoplastic cells in the presence of normal cells. Thus, in a variety of cultures, where androgenic receptor containing cells may be susceptible to becoming or are tumorous, by maintaining a cytotoxic level of a subject compound in the medium, cells may be selectively killed.

In addition, the radiolabeled compounds may be used for therapeutic and/or diagnostic purposes, depending upon the choice of radiolabel. The radiolabeled compounds may be formulated in accordance with conventional ways using physiologically acceptable components, exemplified by various liquid dispersants, such as deionized water, PBS, DMSO, ethanol, etc. in conjunction with various additives, e.g. non-ionic detergents, dextrose, stabilizers, antibiotics, etc. Normally, the radioactive label will be provided immediately prior to use, so that the radioactive product will be prepared at the site or be shipped to the site of the injection. The formulation will normally be administered by intravenous injection.

The following examples are offered by way of illustration and not by way of limitation.

EXPERIMENTAL

EXAMPLES

Example 1

4-nitro-3-trifluoromethyl-N-(2-hydroxy-2-methyl-3-amino-propionyl)aniline (BP-34)

A pressure reactor was charged with 4-nitro-3-trifluoromethyl-N-[2,3-epoxy-2-methyl propionyl]aniline, BP-33, (10.0 g, 34.46 mmol) and methanol (100 mL). After cooling to −70° C., ammonia in excess was condensed into the reactor which was sealed and stirred 14 hours. Following evaporation, the crude solid was washed with cold $CH_2Cl_2$ (5 mL). Filtration and drying gave 6.1 g BP-34 (58% yield).

Melting point: 142–145° C.

Example 2

4-nitro-3-trifluoromethyl-N-(2'-hydroxy-2'-methyl-3'-N-(heptafluorobutyramido)propionyl)aniline (BP-521)

BP-34 (247 mg, 0.80 mmol) under nitrogen with $CH_2Cl_2$ (5 mL), THF (10 mL) and $NEt_3$ (1.1 mL, 0.80 mmol) was cooled to 0° C. and heptafluorobutyryl chloride added (120 μL, 0.80 mmol). After cooling at RT the volatiles were removed. $CH_2Cl_2$ (30 mL) and $H_2O$ (50 mL) were added, the organic layer separated and dried over $MgSO_4$. The product after silica gel ($CHCl_3$/acetone) was isolated as a colorless oil (320 mg, 82% yield).

$^1$H NMR ($CDCl_3$, 500 MHz): δ9.27 (S, Ar—NHC(O); 4.75 (S, C—OH); 3.82 (m, CCH, NH).

Example 3

4-nitro-3-trifluoromethyl-4-N-(2'-hydroxy-2'-methyl-3'-pentadecafluorooctyl amido)-propylamide (BP-562)

To BP-34 (360 mg, 1.17 mmol) was THF (10 mL) and $NEt_3$ (485 μL, 3.5 mmol) were added. The solution was cooled to 0° C. and pentadecyloctanoyl chloride added (295 μL, 1.17 mmol). After reaching RT, the volatiles were removed. After silica gel (CHCl₃/acetone), the product was obtained as a pale yellow solid (689 mg, 84% yield).

Mass spectrum (m/z): 704 (MH$^+$); 726 (M+Na$^+$). $^{19}$F NMR (470 MHz, CDCl$^3$): −56.8 ppm, −77.3, −116.3, −118.1, −118.6, −119.1, −119.4, −122.7.

Example 4

4-nitro-3-trifluoromethyl-N- [2'hydroxy-2'-methyl-3'-N-(heptafluorobutyl)aminopropionyl]aniline (BP-626)

BP-33 (50 mg, 0.172 mmol) was dissolved in THF (1 mL) and 2,2,3,3,4,4,4-heptafluorobutyl amine (200 mg, 1 mmol), and heated at 90° C. for 6 h. After stripping, the solid after silica gel (CH₂Cl₂/acetone), gave BP-626 as an oil. (61 mg, 72% yield)

mass spectrum (m/z): 590 (MH$^+$), 512 (MNa$^+$)

Example 5

2-thioethylheptafluorobutyramide (BP-532)

Heptafluorobutyryl chloride (11.9 g, 51 mmol) was added to a solution of 2-(S-triphenylmethylthio)ethylamine (15.58 g, 49 mmol) and NEt₃ (5.43 g, 54 mmol) in CH₂Cl₂ (50 mL) at 0° C. After 2 h, the reaction was quenched and extracted with H₂O (1×20 mL), saturated NaHCO₃ (20 mL), and saturated NaCl (20 mL). Solvent were evaporated and the residue crystallized from hexane (150 mL) to yield (23.06 g (91.3%).

mp: 99–104° C.

Trifluoroacetic acid (22.16 g, 194 mmol) was added to a solution of the product (10.02 g, 194 mmol) in CH₂Cl₂ (20 mL). After 5 minutes, triethylsilane (5.65 g, 49 mmol) was added. Solvent was evaporated and the solid was purified by silica gel chromatography (CH₂Cl₂) to yield (4.69 g, 88.3%).

Example 6

4-cyano-3-trifluoromethyl-N-[(2'-hydroxy-2'-methyl-3'-S-{(2"-heptafluorobutyramido)ethyl)thio}propionyl)aniline (BP-533)

A solution of BP-532 (1.6 g, 5.9 mmol) in THF (5 mL) was added to a suspension of NaH (0.157 g, 6.6 mmol) in THF (2.6 mL) at 0° C. After 30 min, a solution of 4-cyano-3-trifluoromethyl-N-[2,3-epoxy-2-methylpropionyl]aniline (1.58 g, 5.9 mmol) in THF (5 mL) was added at RT. The reaction was quenched with H₂O and extracted with Et₂O (3×20 mL). Solvent was evaporated and the residue purified by silica gel chromatography (chloroform/acetone) to yield a white, crystalline solid (2.55 g, 79.9% yield).

Example 7

4-cyano-3-trifluoromethyl-N-(2'-hydroxy-2'-methyl-3'-S{2"-heptafluorobutyramido)ethyl) sulphinylipropionyl)aniline (BP-567+BP-568)

A solution of sodium metaperiodate (0.18 g, 0.86 mmol) in water (10 mL) was added dropwise to a solution of BP-533 (0.39 g, 0.72 mmol) in MeOH (15 mL) at RT. After stirring for 14 h, the filtered solid was washed with MeOH (15 mL). Volatiles were evaporated in EtOAC (100 mL) and extracted with water (10 mL), 10% aq. sodium sulfite (15 mL) and then saturated NaCl (15 mL). The organic layer was dried over MgSO₄ and solvent was evaporated. The residue was purified by silica gel chromatography (50:50 CHCl₃/acetone) to yield two diastereomers as white, crystalline solids (0.31 g, 78.0%).

Example 8

4-cyano-3-tri-fluoromethyl-N-[(2'-hydroxy-2'-methyl-3'-S-{(2"-heptafluorobutyramido)ethyl) sulfonylipropionyl)aniline (BP-534)

A solution of MCPBA (0.796 g, 4.6 mmol) in CH₂Cl₂ (100 mL) was added dropwise to BP-533 (1.09 g, 2.01 mmol) in CH₂Cl₂ (100 mL). After stirring for 14 h, the reaction was quenched with 10% aq. sodium sulfite (20 mL), extracted with Na₂CO₃ (2×15 mL), and brine (15 mL). Solvent was evaporated and the residue purified by silica gel chromatography (CHCl₃/acetone) to yield the product as an oil (0.93 g, 79.8%).

Example 9

4-[2'-5'-dioxo-3',3'-dimethyl-1'-pyrrolidinyl]-2-trifluoromethyl-benzonitrile (BP-245)

2,2-dimethyl succinic anhydride (34.41 g, 268 mmol) was placed in a flask and melted at 140° C. under nitrogen. 5-amino-2-trifluoromethyl benzonitrile (25 g, 134 mmol) was added in portions, followed by methanesulfonic acid (500 μL). After two h, temperature was reduced to 120° C. and EtOAc (200 mL) was added. The solution was washed with NaHCO₃ (2×50 mL), then saturated NaCl (50 mL). Drying (MgSO₄), filtration, and removal of the solvents left an oil, which was dissolved in toluene (200 mL) at 60° C. After several days, filtration and drying yielded BP-245 (25.7 g, 65%) as colorless crystals.

HPLC purity=99%, melting point: 131–33° C.

Example 10

4-[2',5'-dioxo-3',3',4'-trimethyl-1'-pyrrolidinyl]-2-trifluoromethyl-benzonitrile (BP420)

BP-245 (10 g, 34 mmol) was dissolved in DMF (40 mL) and THF (20 mL) in a Schlenk flask and cooled to −78° C. under nitrogen. Lithium bis(trimethylsilyl)amide (34 mL, 1 M in THF; 34 mmol) was added over 10 minutes, iodomethane (5.1 g, 35.7 mmol) in THF (20mL). The reaction was allowed to warm to RT and stirred for 12 h. The reaction was poured into toluene (400 mL), 1N HCl (200 mL), the layers separated and the toluene layer washed with 50% saturated NaCl (100 mL). Drying (MgSO₄), filtration and solvent removal gave a yellow, crystalline solid, which was purified by silica gel (toluene/acetone) and crystallized from toluene (40 mL) to yield a white, crystalline solid. (2.19 g, 21% yield).

Example 11

4-[2',5'-dioxo-3',3',4',4'-tetramethyl-1'-pyrrolidinyl]-2-trifluoromethyl-benzonitrile (BP-424)

BP-245 (5.0 g, 16.9 mmol) was dissolved in dry DMF (22 mL) and cooled to −60° C. Lithium bis(trimethylsilyl)amide (33.8 mL 1 M in THF; 33.8 mmol) was added over 10 minutes, followed by iodomethane (5.025 g, 35.4 mmol) in THF (10 mL). After 6 h at −20° C., mixture was poured into toluene (200 mL) 1 N HCl (100 mL). The layers were separated and the toluene layer washed with saturated NaCl (50 mL). Drying (MgSO₄), filtration and solvent removal gave an oil, which was purified on silica gel (toluene/acetone). Yield of BP-424=3.25 g (60%)
melting point: 162.5–164° C.

Example 12

4-[2'-oxo-5'-hydroxy-3',3',4',4'-tetramethyl-1'-pyrrolidinyl]-2-trifluoromethyl-benzonitrile (BP-511)

BP-424 (100 mg, 0.31 mmol) was dissolved in methanol (2 mL) and 1 N HCl (100 uL). At 15° C., solid sodium borohydride (58 mg, 1.54 mmol) was added over 2 minutes. After 14 h at RT, methanol was removed, and the product partitioned between EtOAc (20 mL) and 10% NaCl (25 mL). The layers were separated, the organic layer washed with saturated NaCl (25 mL) and dried (MgSO$_4$), and evaporated to give a white solid (109 mg) which was further purified by crystallization from CH$_2$Cl$_2$. (88 mg, 87% yield)

Melting point: –195–197° C. Mass spectrum (m/z): 325 (MH+)MW=326.32

Example 13

4-(2'-oxo-5'-heptafluorobutyloxy-3',3',4',4',-tetramethyl-1'pyrrolidinyl)-2-trifluoromethyl benzonitrile (BP-569)

BP-511 (100 mg, 0.036 mmol) was suspended in 2,2,3,3,4,4,4-heptafluorobutanol (1 mL) and methanesulfonic acid (100 uL) and was stirred at RT for 6 h. The solution was poured into 0.1 M K$_2$HPO$_4$ (pH 7.0, 15 mL) and EtOAc (25 mL).

The organic layer was washed with brine (2×10 mL) and dried (MgSO4). Stripping and silica gel chromatography (CCl$_4$/acetone) gave a white solid (53 mg, 34% yield).

Mass spectrum (m/z): 509 (MH$^+$)

Example 14

4-[3'-(4"-N-t-butoxycarbonyl)-aminobutyl)-4',4'-dimethyl-5'-imino-2'thioxo-1'-imidazolidinyl]-2-trifluoromethyl-benzonitrile (BP-380)

4-cyano-3-trifluoromethyl phenylisothiocyanate (2.3 g, 10 mmol) was dissolved in THF (15 mL), and NEt3 (1.43 mL, 10.3 mmol) then added to crude 2-(1',4'-butylamino-N-tbutoxy-carbonyl)-2-cyanopropane (2.6 g, 10.2 mmol) in THF (10 mL). After 1.5 h, the volatiles were removed in vacuo. Silica gel column (CHCl$_3$/acetone) gave a yellow solid (3.6 g) 94% pure by HPLC.

$^1$H NMR (500 MHz, CDCl$_3$): δ3.20 (m, 2H, CH$_2$NHC (O)); 3.68 (m, 2H, CH$_2$NC(S)).

Example 15

4-[3'-(4"-aminobutyl)-4',4'-dimethyl-5'-imino-2'thioKo-1'imidazolidinyll-2trifluoromethyl-benzonitrile (BP-381)

BP-380 (21.0 g, 44 mmol) was dissolved in MeOH (80 mL). 4 N HCl (40 mL, 160 mmol) and methanol (40 mL) were added. After reflux for 1.5 h and evaporated. The product was filtered from an EtOH slurry, washed with cold EtOH (50 mL) and dried under vacuum to give a colorless solid (15.8 g, 88.5% yield).

$^1$H NMR (DMSO-d$_6$, 500 MHz): δ3.72 (m, 2H NCH$_2$CH$_2$); 2.82 (m, 2H, CH$_C$CH$_2$NH$_3$); 1.55 (s, 6H, CCH$_3$).

Example 16

4-[3'-(4"-heptafluorobutyramidobutyl)-4',4'-dimethyl-5'oxo-2'-thioxo-1-imidazolidinyl]-2-trifluoromethyl-benzonitrile (BP-443)

BP-381 (15.8 g, 37.6 mmol) was placed in a flask with CH$_2$Cl$_2$ (200 mL) and NEt$_3$ (23 mL, 165 mmol). Heptafluorobutyryl chloride was added (6.2 mL, 41.3 mmol). After stirring for 6 h at RT and everything followed by silica gel (CHCl$_3$/acetone). An oil (8.9 g) resulted (41% Yield).

$^{19}$F NMR(CDCl$_3$); –58.5 ppm (ArCF$_3$); –77.1 (CF$_2$CF$_3$); –117.2 (C(O)CF$_3$);-123.4 (CF$_2$CF$_2$CF$_3$). $^{13}$C NMR (CDCl$_3$127 MHz): 157.8 175.13, 178.55 ppm.

Example 17

4-[3'-((4"-heptaflurobutylamidoethyl)butyl)-4',4'-dimethyl-5'-imino-2'-thioxo-1'-imidazolidinyl]-2-trifluoromethyl benzonitrile (BP444)

BP-138 (340 mg, 0.95 mmol; acc. to example 7) was dissolved in CH$_2$Cl$_2$ (5 mL) and NEt$_3$ (0.397 mL, 2.85 mmol). Heptafluorobutyryl chloride was added (0.142 mL, 0.95 mmol). After 30 minutes at RT, the volatiles were removed. Silica gel (CHCl$_3$/acetone) gave a colorless solid (280 mg) (5% Yield).

$^{19}$F NMR (470 MHz, CDCl$_3$): –58.6 ppm, –77.0,–117.0, –123.3.

Example 18

N-(4-cyano-3-trifluoromethyl-phenyl)-N'-heptafluorobutyl)thiourea (BP-628)

4-cyano-3-trifluoromethyl phenylisothiocyanate (2.28 g, 10 mmol) was dissolved in THF (15 mL), and cooled to 5° C. 2,2,3,3,4,4-heptafluorobutyl amine (209 mg, 10.5 mmol) was added after stirring for 1 h, with EtOAc (60 mL) and 1 N HCl (25 mL) were added. The organic layer was washed with saturated NaCl (15 mL) and dried (MgSO$_4$). Silica gel chromatography (CH$_2$Cl$_2$/acetone), gave a white solid (90% yield).

Example 19

4-nitro-3-trifluoromethyl-N-[2'-hydroxy-2'-methyl-3'-{N'-(methyl)-N'-(3"-phenyl-3"-(p-trifluoromethyl phenyl))propyl}amino}aniline (BP-657)

BP-33 (77 mg, 0.264 mmol) and fluoxetine (68 mg, 0.22 mmol) were dissolved in p-dioxane (3 mL) and the solution heated for 6 h at 95° C. The solvent was removed and the product purifed on silica gel (CH$_2$Cl$_2$/MeOH/NEt$_3$). Yield= 64 mg (48% Yield).

Example 20

2-hydroxy-3-((2-hydroxy-2-(N-(4-nitro-3-(trifluoromethyl)phenyl)carbamoyl)propyl)amino)-2-methyl-N-(4-nitro-3-(trifluoromethyl)phenyl) propanamlde (BP-673)

BP-33 (1.0 g, 34 mmol) was dissolved in methanol (40 mL). NH$_4$OH (30%, 4 mL) was added and the reaction stirred at room temperature for 24 h. The volatiles were removed and the crude solid chased with methanol (2×10 mL). The product was collected as a precipitate from methylene chloride and further purified using column chromatography (CH$_2$Cl$_2$/MeOH gradient) to give a yellow solid. Yield of BP-673=490 mg (48%).

Mass Spectrum (m/z): MH$^+$598.

Example 21

2-hydroxy-3-((2-(2-(2-hydroxy-2-(N-(4-nitro-3-(trifluoromethyl)phenyl)carbamoyl)propyl)amino) ethoxy)ethoxy)ethyl)amino)-2-methyl-N-(4-nitro-3-(trifluoromethyl)phenyl)propanamide (BP-676).

BP-33 (500 mg, 1.72 mmol) was placed in flask with stir bar. Dioxane was added. In a separate flask, dissolved diamine (Hunstman XTJ-504) (127 mg, 0.86 mmol) in Dioxane (4 mL). This was added to the former and the resulting solution was stirred and heated at 90° C. for 5 h. The oil bath was removed and the reaction stirred for 9 h. at room temperature. The volatiles were removed and chloroform added (10 mL), to give a colorless precipitate, which was collected and dried to give the product as a colorless solid. Yield of BP-676=290 mg (46%).

Mass Spectrum (m/z): MH$^+$=729

Example 22

N-(4-chlorophenyl)-3-((2-(N-(4-chlorophenyl) carbamoyl)-2-hydroxypropyl)amino)-2-hydroxy-2-methylpropanamide (BP-708)

BP-706 (3.0 g, 14.2 mmol) was dissolved in CH$_3$OH in flask and stir bar. NH$_4$OH (12 mL) was added turning solution into yellow liquid. After stirring two days, the volatiles were removed and the crude product chased with MeOH (2×120 mL). The product was purified using column chromatography (CH$_2$Cl$_2$: MeOH gradient) and isolated to produce white crystals. Yield of BP-708=2.56 g (41%).

Mass Spectrum (m/z): MH$^+$=440 mp. 76–78° C.

Example 23

3-((((4-bromophenyl)amino)thioxomethyl)amino)-2-hydroxy-2-methyl-N-(4-nitro-3-(trifluoromethyl) phenyl)propanamide (BP-668)

BP-34 (2.0 g, 6.5 mmol) was dissolved in anhydrous THF (30 mL) under N$_2$(g). NEt$_3$ was added (100 $\mu$L). In a separate flask under N$_2$(g), 4-bromophenylisothiocyanate was similarly added to the former mixture. After stirring for 1 h, the volatiles were removed and the crude product purified via silica gel column chromatography (CHCl$_3$/acetone gradient) to give the product as a yellow solid (m.p. 192–195° C.) in 67% yield.

Mass Spectrum (m/z): MH$_+$=521, 523

Example 24

3-((((cyclohexylmethyl)amino)thioxomethyl)amino)-2-hydroxy-2-methyl-N(4-nitro-3-(trifluoromethyl) phenyl)propanamide (BP-743)

BP-34 (2.0 g, 6.5 mmol) was dissolved in anhydrous THF (30 mL) under N$_2$(g). NEt$_3$ was added (2.7 mL) and then followed by cyclohexylmethylisothiocyanate (1.0 g, 6.4 mmol). After stirring for 3 h, the volatiles were removed and product purified via silica gel column chromatography (CH$_2$Cl$_2$: acetone gradient) to give a yellow solid (m.p. 77–81° C.) in 84% yield.

Mass Spectrum (m/z): MH$^+$=463; MNa$^+$=485.

Example 25

4-[2',5'-dioxo-3',3',4'-trimethyl-4'-propynyl-1'-pyrrolidinyl]-2-trifluoromethyl-benzonitrile (BP-535)

BP-420 (1.71 g, 5.5 mmol) was placed in a flask. After cooling to −50° C., lithium bis(trimethylsilyl)amide (5.55 mL, 1 M in THF; 5.55 mmol) was added, followed by propargyl bromide (0.69 g, 58 mmol). The reaction was held at 0° C. overnight after which it was poured into 1 N HCl (30 mL) and extracted with EtOAc. The organic layer was washed with 50% saturated NaCl (100 mL). Drying (MgSO$_4$), filtration and solvent removal gave a solid, which was purified on silica gel (toluene/acetone). The product was re-crystallized from toluene (1.05 g, 55% yield).

Example 26

2-(trifluoromethyl)-4-(3,3,4-trimethyl-2,5-dioxo-4-(6,7,7-trifluorohept-6-en-2-ynyl)cyclopentyl) benzenecarbonitrile (BP-751)

BP-535 (120 mg, 0.34 mmol) is dissolved in anhydrous THF (10 mL) and the solution cooled to −78° C. KN(SiMe$_3$)$_2$ (344$\mu$L, 1 M in toluene) is added, followed by BrCH$_2$CH$_2$CF=CF$_2$ (65 mg, 0.34 mmol). The solution is allowed to warm to RT, is quenched with 1 N HCl and extracted with EtOAc. The layers are separated and the organic layer dried (MgSO$_4$), filtered and concentrated to give the crude product, which is purified via column chromatography to give the product as a colorless solid.

Example 27

4-cyano-3-trifluoromethyl-N-(2'-hydroxy-2'-methyl-3'-N-(heptafluorobutyramido)propionyl)aniline (BP-713)

BP-646 (the cyano analog of BP-34)(1.121 g, 3.89 mmol) was dissolved in dry CH$_2$Cl$_2$ and NEt$_3$ (1.6 mL) was aded. Heptafluorobutyryl chloride was added (558 $\mu$l, 4.28 mmol). After 3 h, volatiles were removed and the product purified by silica gel chromatography (CH$_2$Cl$_2$/acetone) to give a colorless solid (1.03 g, 55% yield)

Mass spectrum (m/z): 482(MH$^+$). Melting point 142–144° C.

Example 28

N-(3-trifluoromethyl-4-cyanophenyl), N'-propyl thiourea (BP-735)

4-Cyano-3-trifluoromethylphenylisothiocyanate (1 g., 4.39 mmol) was dissolved in anhydrous THF (30 mL) and cooled to 0° C. n-Propylamine was added slowly and the ice bath removed. After stirring at RT for 16 h, volatiles were removed and the product was crystallized from toluene to give off-white plates (1.02 g, 77% yield).

Example 29

2-hydroxy-3-(((4'-iodophenyl)amino) carbonylamino)-2-methyl-N-(4"-nitro-3"-trifluoromethyl)phenyl)propanamide (BP-754)

BP-34 (2.35 g., 7.66 mmol) was dissolved in anhydrous THF (25 mL). In a separate flask, p-iodophenylisocyanate (2.0 g., 8.16 mmol) was dissolved in anhydrous THF (10 mL). NEt$_3$ (3.2 mL) was added to the first solution, followed by addition of the isocyanate solution. After 2 h, the volatiles were removed and the crude product washed with CH$_2$Cl$_2$ (2×50 mL) and the resulting product collected as a pale yellow solid (4.0 g., 95% yield).

Example 30

4-[3'-trans-(2"-propenyl-3"-iodo)-4',4'-dimethyl-5'-oxo-2'-thioxo-1'-imidazolidinyl]-2-trifluoromethylbenzonitrile (BP-305); 4-[3'-cis-(2"-propenyl-3"iodo)-4',4'-dimethyl-5'-oxo-2'-thioxo-1'-imidazolidinyl]-2-trifluoromethylbenzonitrile (BP-305)

BP-199 (4-[4',4'-dimethyl-3-propargyl-5'-oxo-2'-thioxo-1'-imidazolidinyl]--2-trifluoromethylbenzonitrile; see WO97/00071) was dissolved in dry toluene (100 mL) under $N_2$. $Bu_3SnH$ (1.12 mL) and AIBN (68.5 mg) were added and the reaction mixture heated to reflux. After stirring for 3 h at reflux, the reaction was allowed to cool to rt and the volatiles removed under vacuum. The crude product was purified by column chromatography ($SiO_2$, eluent $CHCl_3$) isolated as a pale oil (1.67 g). Purity 95.3% HPLC.

BP-237 (80:20 E/Z isomers, 370 mg) was dissolved in $CHCl_3$ (5 mL) and cooled to 0° C. In a separate flask, $I_2$ (146 mg) was dissolved in $CHCl_3$ (15 mL) and added to the solution of BP-237. After 2 h at rt, the volatiles were removed and the product mixture purified using silica chromatography (gradient $CHCl_3$/acetone). BP-305 (trans isomer) was isolated as a whhite crystalline solid 200 mg, m.p. 137–139° C. Purity was 96.4% (contaminated with 1.2% of BP-307 (HPLC)). Pure BP-307 was obtained by further use of column chromatography (70 mg, m.p. 146–7° C., purity 99.2%:HPLC)

Example 31

4-cyano-3-trifluoromethyl-N-[2'-hydroxy-2'-methyl-3'-(propargyloxypropionyl]aniline (BP-632)

To a solution of propargyl alcohol (2.59 mL, 44.5 mmole) cooled to −78° C. was added dropwise a solution of methyl lithium in diethyl ether (27.8 mL, 1.6M). After 30 min a solution of 4-cyano-3-trifluoromethyl-N-[2,3-epoxy-2-methylpropionyl]aniline (4.0 g, 14.8 mmole; prepared according to the general method in EP 0 100 172) in THF (40 mL) was added. The solution was allowed to reach rt, stirred 20 h and the volatiles removed. The residue was partitioned between THF/sat. aq. NaCl (50 mL/50 mL), the organic layer concentrated under reduced pressure to an oil and purified by silica chromatography ($CHCl_3$/acetone) to yield 4.27 g (88%) BP-632.

Example 32

4-cyano-3-trifluoromethyl-N-[2'-hydroxy-2'-methyl-3'-[3"-($^{125}$I)iodo-trans-2"-propenyloxy]propionyl aniline (BP-636): 4-cyano-3-trifluoromethyl-N-[2'-hydroxy-2'-methyl-3'-[3"-($^{125}$I)iodo-cis-2"-propenyloxy]propionyl aniline (BP-637); 4-cyano-3-trifluoromethyl-N-[2"-hydroxy-2'-methyl-3'-[gem-di-3"-($^{125}$I)iodo-2"-propenyloxy]propionyl aniline (BP-638)

A. 4-cyano-3-trifluoromethyl-N-[2'-hydroxy-2'-methyl-3'-[3"-tributylstannyl-trans-2"-propenyloxy]propionyl aniline (BP633): 4-cyano-3-trifluoromethyl-N-[2'-hydroxy-2'-methyl-3'-[3"-tributylstannyl-cis-2"-propenyloxy]propionyl aniline (BP-634); 4-cyano-3-trifluoromethyl-N-[2'-hydroxy-2'-methyl-3'-[gem-di-tributylstannyl-2"-propenyloxy]propionyl aniline (BP-635)

To a solution of BP-632 (2.60 g, 8.0 mmole) in toluene (30 mL) was added BuSnH (3.21 mL, 12.0 mmole) and AIBN (1.39 g, 12.0 mmole). The solution was refluxed for 20 h, the volatiles removed and the crude product purified on silica chromatography ($CHCl_3$/acetone) to yield 4.07 g (89%) of an 8:1:1 mixture of trans, cis and gem isomers (BP-633, -634, -635)

B. The mixture prepared above is dissolved in a small amount of DMF. Radioiodination is accomplished using $Na[^{123}]I$, $Na[^{125}]I$ or $Na[^{131}]I$ by known methods. (See Hunter and Greenwood, Nature (1962) 194:495–6)

Example 33

4-cyano-3-trifluoromethyl-N-[2'-hydroxy-2'-methyl-3'-[3"-($^{125}$I)iodo-trans-2"-propenylthio]propionyl aniline (BP-552): 4-cyano-3-trifluoromethyl-N-[2'-hydroxy-2'-methyl-3'-[3"-($^{125}$I )iodo-cis-2"-propenylthio]propionyl aniline (BP-553); 4-cyano-3-trifluoromethyl-N-[2'-hydroxy-2'-methyl-3'-[gem-di-3"-($^{125}$I)iodo-2"-propenylthio]propionyl aniline (BP-554)

A. A solution of propargylthiol (100 mL, 0.13M in THF/$CH_2Cl_2$; prepared according to Castro, J. et al., Synthesis 1977, 518) was added ot a suspension of NaH (0.52 g, 13.0 mmole, 60% in oil) in THF (25 mL) at −78° C. and stirred for 1 h. To this cold solution was added a solution of 4-cyano-3-trifluoromethyl-N-[2,3-epoxy-2-methylpropionyl]aniline (3.51 g, 13.0 mmole; prepared according to EP 0 100 172 general method) in THF (20 mL) and stirred 1 h at −78° C. The solution was allowed to reach rt, stirred 1 h and the volatiles removed. The residue was partitioned between $CHCl_3$/$H_2O$ (200 mL/200 mL), the organic layer concentrated to an oil under reduced pressure and purified by silica chromatography ($CH_2Cl_2$) to yield 1.13 g (25%) BP-548

B. 4-cyano-3-trifluoromethyl-N-[2'-hydroxy-2'-methyl-3'-[3"-tributylstannyl-trans-2"-propenylthio]propionyl aniline (BP-549): 4-cyano-3-trifluoromethyl-N-[2'-hydroxy-2'-methyl-3'-[3"-tributylstannyl-cis-2"-propenylthiolpropionyl aniline (BP-550); 4-cyano-3-trifluoromethyl-N-[2'-hydroxy-2'-methyl-3'-[gem-2"-di-3"-tributylstannyl-2"-propenylthiolpropionyl aniline (BP-551)

BP-548 (1.03 g, 30 mmole) was dissolved in 1,4-dioxane (15 mL) and toluene (30 mL). $Bu_3SnH$ (1.21 mL, 4.5 mmole) and AIBN (0.52 g, 4.5 mmole) were added and the reaction mixture hreated to reflux for 12 h. The volatiles were removed and the crude product was purified on silica chromatography ($CHCl_3$) to yield 0.78 g (44%) of a 5:3:2 mixture of the gem, cis and trans isomers. (BP-551, -550, and -549, respectively).

C. The mixture of BP-549, -550 and -551 prepared above is dissolved in a small amount of DMF. Radioiodination is accomplished using $Na[^{123}I, Na[^{125}]I$ or $Na[^{131}]I$ by known methods. (See Hunter and Greenwood, Nature (1962) 194:495–6).

Compounds were tested for stability in human serum at 38° C. They were dissolved in isopropanol/$H_2O$ (95:5), mixed with human serum to a concentration of 0.5 mg/mL, and incubated at 38° C. Serum aliquots were extracted with ethyl acetate and analyzed by HPLC. In an accelerated stability study of the compounds BP-521, BP-668, BP-673 and BP-735, formulated in isopropanol/$H_2O$ (95:5) and incubated at 50° C., no change was observed via HPLC up to six days.

TABLE 1

Percent of the intact compound remaining in human serum at 38° C. after incubation.

| Compound | 6h | 24h | 48h | 6d |
|---|---|---|---|---|
| BP-521 | 97.5 | 90.0 | 84.0 | 60.0 |
| BP-668 | — | 100 | 100 | 100 |
| BP-673 | — | 100 | 100 | 100 |
| BP-735 | — | 100 | 100 | 100 |

It can be seen that BP-521 has a limited stability resulting from hydrolysis of the perfluoroamide, leaving the free amine, BP-34 (Example 1) and the perfluorocarbon moiety. Compounds BP-673 (a dimeric species), BP-668 and BP-735 have proved stable.

Sufficiently stable compounds were dissolved in EtOH/DMSO and incubated with human prostate cancer cells LNCaP, which contain AR. After 72 h, an XXT assay (Scudievo, et al., Cancer Research, 48:4827 (1988)) indicating cell viability was carried out. Table 2 shows the lowest drug concentrations needed to abolish 50% of the cellular viability.

TABLE 2

Effect on cell viability

| Compound: | Molar Concentration: |
|---|---|
| Bicalutamide | $7.0 \times 10^{-5}$ |
| Hydroxyflutamide | $5.0 \times 10^{-5}$ |
| BP-34 | $<1 \times 10^{-4}$ |
| BP-443 | $5.5 \times 10^{-6}$ |
| BP-463 | $5.5 \times 10^{-5}$ |
| BP-483 | $6.25 \times 10^{-6}$ |
| BP-521 | $5.6 \times 10^{-6}$ |
| BP-546 | $4 \times 10^{-6}$ |
| BP-668 | $1.5 \times 10^{-5}$ |
| BP-673 | $2.7 \times 10^{-5}$ |
| BP-676 | $1.4 \times 10^{-5}$ |
| BP-713 | $1 \times 10^{-5}$ |
| BP-735 | |

The interaction of the compounds with AR was studied by incubation with LNCaP cells, subsequent cell lysis and the standard Western Blot assay. Table 3 shows percent of remaining AR contained in the lysate following incubation of the cells with test compounds for 48 h.

TABLE 3

Percent of the androgen receptor remaining in human prostate cancer cells, LNCaP, by Western Blot.

| Compound: | @ 3μMolar conc.: | @ 10μMolar conc.: |
|---|---|---|
| BP-34 | 97 | 98 |
| BP-521 | 38 | 0 |
| BP-562 | 33 | 12 |
| BP-668 | 73 | 0 |
| BP-673 | 74 | 3 |
| BP-676 | 64 | 20 |
| BP-713 | 50 | 3 |
| BP-735 | 45 | 1 |
| BP-754 | 28 | 14 |
| Bicalutamide | 97 | 89 |
| Hydroxyflutamide | 98 | 94 |

It can be seen that not all compounds which showed strong inhibition of LNCaP cells, by XXT assay, were also active in suppressing the AR. Unlike the control antiandrogens, i.e. hydroxyflutamide and bicalutamide, compounds BP-521, BP-673, BP-668, BP-713 and BP-735 practically eliminated the AR at 10 μM concentration.

The free amine, BP-34, a product of the decomposition of BP-521, had no effect on the AR, nor on the LNCAP cells.

Bioavailability results of BP-521 are shown in Table 4.

TABLE 4

Bioavailability of BP-521

| Species | Applic./dose in mg/kg bw | μg/ml blood at h.: 0.5, 1.0, 7.0, 24, 1.5, 2.5 | | | | | | mg/total blood volume and dose % | |
|---|---|---|---|---|---|---|---|---|---|
| Rabbit ~3 kg | oral, 100 | 1.5 | 1.7 | 2.6 | 1.5 | 1.0 | 1.0 | 3.0μg | 1.50% |
| Rabbit ~3 kg | i.p., 150 | 1.9 | 3.2 | 1.9 | 1.5 | 3.0 | 2.2 | 11.6μg | 2.8% |
| Rabbit ~3 kg | topical skin 20 cm² 33 | 0 | 0 | 0 | 0 | 0 | 0 | 0 | 0 |
| Rat ~140 g | i.m., 75 | 0.7 | 4.7 | 2.2 | — | — | 1.0 | 2.1μg | 2.9% |

Only a fraction of the dose is systemically available upon oral, i.p., s.c. or i.m. application. The peak serum levels in the oral test was 0.0052% of the injected dose, as compared to the 0.03% reported for bicalutamide (Cockshott ID, et al. *Eur Urol.* 1990, Vol 18, Suppl. 3: 10–17).

When male rats were given 10 times subcutaneously 100 mg/kg of BP-521, the average weight of their prostate and seminal vesicles was reduced by about 46%. On the other hand, 0.1 mg/kg dose of BP-521 or BP-668 in castrated rats supplemented with testosterone propionate did not reduce the secondary sex organs' weight, while 0.5mg/kg of bicalutamide did, by about 20%. (The dose of 0.1 mg/kg approximates the expected topical daily dose for humans).

In topically treated rabbits, 2× daily with 0.5 mL of a 10% solution of BP-521 in 50/50 PEG 400/EtOH over a shaved skin area of 20 cm², no absorption was found by HPLC with sensitivity of detection of 10 nanograms.

Systemic toxicity was orientationally evaluated by i.p. injection every 2nd day in mice. BP-521, 200 mg/kg bw was given 5 times, without mortality or morbidity, while morbidity but no mortality was seen at 350 mg/kg bw. For BP-34, the corresponding values were 150 mg/kg bw and 300 mg/kg bw.

In an orientational test on five male volunteers, 1% solution of BP-521 in isopropanol, 0.5 mL applied twice daily on the affected scalp, effectively arrested incipient hair loss of the forehead line and after 8 weeks, induced copious growth of vellus hair.

BP-521, due to the low systemic toxicity, lack of absorption from skin and degradability, is suitable for treatment of skin disorder. The resulting decomposition products have no antiandrogenic activity, and the other decomposition product and perfluorobutyric acid, was shown to have low toxicity (Takagi A, et al. *Cancer Letters.* 1991, 57: 55–60).

Compounds containing non-radioactive iodine (BP-554, -636 and -305) were shown to interact with AR by Western blots. They were formulated in ethanol, DMSO, Tween and dextrose in water and injected intravenously into male nude mice bearing a human prostate cancer tumor. After 4 h the mice were sacrificed and iodine determined in blood, prostate, kidney, liver and the tumor relative. There was substantial iodine accumulation in the prostate and the tumor vis-a-vis the other tissues. As described in U.S. Pat. No. 5,656,651, the subject compounds can be used for whole body scanning to depict prostate cancer and metastases.

It is evident from the above results that compounds are provided which are effective with indications associated with the androgen receptor, such as androgen dependent tumors, and skin androgen mediated disorders, such as acne, hirsutism and androgenetic alopecia. In addition to having cytotoxic and cytostatic activity, some of the compounds demonstrate androgen receptor suppression. For topical treatment, compounds are provided which have low resorption.

Although the foregoing invention has been described in some detail by way of illustration and example for purposes of clarity of understanding, it will be obvious that certain changes and modifications may be practiced within the scope of the appended claims. All references cited herein are incorporated herein by reference, as if set forth in their entirety.

What is claimed is:

1. A compound of the formula:

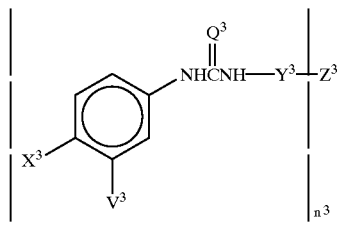

wherein:
 $X^3$ is nitro or cyano;
 $V^3$ is $CF_3$;
 $n^3$ is 1 or 2;
 $Q^3$ is chalcogen;
 when n is 1, $Y^3$ is a bond or linking group of a total of from 1 to 6 atoms, which are C, N, O and S; and
 $Z^3$ is polyfluoroacylamido of from 2 to 6 carbon atoms and at least 2m–2 fluorine atoms, wherein m is the number of carbon atoms, or haloanilino, where halo is of atomic number from 9 to 80;
 when n is 2, $Y^3$ and $Z^3$ are taken together to form a linking group of a total of 1 to 0 C., N, O, and S atoms.

2. A compound according to claim 1 of the formula N-(3-trifluoromethyl-4-cyanophenyl), N'-propyl thiourea.

3. A method of treating an indication dependent upon activation of the androgen receptor, said method comprising:
 administering an effective amount to inhibit said activation of a compound according to claim 1.

4. A method according to claim 3, wherein said indication is a hyper-androgenic skin syndrome and said administering is topical.

5. A method according to claim 3, wherein said indication is cancer and said administering is systemic.

6. A pharmaceutical formulation for treatment of an indication dependent upon activation of the androgen receptor comprising a compound of the formula:

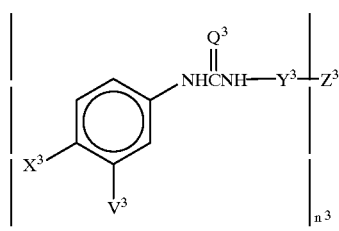

wherein:
 $X^3$ is nitro or cyano;
 $V^3$ is $CF_3$;
 $n^3$ is 1 or 2;
 $Q^3$ is chalcogen;
 when n is 1, $Y^3$ is a bond or linking group of a total of from 1 to 6 atoms, which are C, N, O, and S; and
 $Z^3$ is alkyl of from 1 to 6 carbon atoms, polyfluoroacylamido of from 2 to 6 carbon atoms and at least 2m–2 fluorine atoms, wherein m is the number of carbon atoms, or haloanilino, where halo is of atomic number from 9 to 80;
 when n is 2, $Y^3$ and $Z^3$ are taken together to form a linking group of a total of 1 to 10 C., N, O, and S atoms, and a pharmacologically acceptable carrier.

7. A method of treating alopecia, said method comprising:
 treating a host suffering from alopecia with a pharmacologically effective amount of a combination of a compound according to claim 1 and a second agent for treating alopecia,
 whereby said alopecia is alleviated.

* * * * *

UNITED STATES PATENT AND TRADEMARK OFFICE
CERTIFICATE OF CORRECTION

PATENT NO. : 6,184,249 B1 Page 1 of 2
DATED : February 6, 2001
INVENTOR(S) : Milos Sovak, Allen L. Seligson, James Gordon Douglass, III, Brian Campion and Jason W. Brown It is certified that error appears in the above-identified patent and that said Letters Patent is hereby corrected as shown below:

<u>Column 4,</u>
Line 33, after "n is 1 or" delete "2and d is 0or 1" and insert -- 2 and d is 0 or 1 --.

<u>Column 7,</u>
Line 13, "hirsutisim" should read -- hirsutism --.

<u>Column 8,</u>
Line 50, "heptafluorobutryl" should read -- heptafluorobutyryl --.

<u>Column 9,</u>
Line 9, "4-nitro-3-trifluoromethyl-N-[2'hydroxy-2'-methyl-" should read
-- 4-nitro-3-trifluoromethyl-N-[2'-hydroxy-2'-methyl- --.

<u>Column 11,</u>
Line 22, "-tetramethyl-1'pyrrolidinyl)-2-trifluoromethyl" should read
-- tetramethyl-1'-pyrrolidinyl)-2-trifluoromethyl --.
Line 36, "dimethyl-5'-2'thioxo-1'-imidazolidinyl]-2-" should read
-- dimethyl-5'-2'-thioxo-1'-imidazolidinyl]-2- --.
Line 50, "2'thioKo-1'imidazolidinyll-2trifluoromethyl-" should read
-- 2'-thioxo-1'-imidazolidinyl-2-trifluoromethyl- --.

<u>Column 12,</u>
Line 42, "purifed" should read -- purified --.
Line 49, "propanimlde (BP-673)" should read -- propanimide (BP-673) --.

<u>Column 14,</u>
Line 26, "aded" should read -- added --.

<u>Column 15,</u>
Line 14, "whhite" should read -- white --.

<u>Column 16,</u>
Line 13, "ot" should read -- to --.
Line 35, "hreated" should read -- heated --.

UNITED STATES PATENT AND TRADEMARK OFFICE
CERTIFICATE OF CORRECTION

PATENT NO. : 6,184,249 B1
DATED : February 6, 2001
INVENTOR(S) : Milos Sovak, Allen L. Seligson, James Gordon Douglass, III, Brian Campion and Jason W. Brown It is certified that error appears in the above-identified patent and that said Letters Patent is hereby corrected as shown below:

Column 19,
Line 33, "n" should read -- $n^3$ --.
Line 36, "1 to 10 C.," should read -- 1 to 10 C, --.
Line 40, "1 to 0 C.," should read -- 1 to 10 C, --.

Column 20,
Line 28, "n" should read -- $n^3$ --.
Line 35, "n" should read -- $n^3$ --.
Line 36, "1 to 10 C., N, O, and S atoms, and" should read -- 1 to 10 C, N, O, and S atoms; and --.

Signed and Sealed this

Sixth Day of August, 2002

Attest:

Attesting Officer

JAMES E. ROGAN
Director of the United States Patent and Trademark Office